United States Patent [19]
Riordan et al.

[11] Patent Number: 5,639,787
[45] Date of Patent: Jun. 17, 1997

[54] THERAPEUTIC METHOD FOR THE TREATMENT OF CANCER

[75] Inventors: Neil H. Riordan; Hugh D. Riordan, both of Wichita, Kans.

[73] Assignee: The Center for the Improvement of Human Functioning Int'l, Inc., Wichita, Kans.

[21] Appl. No.: 397,663

[22] Filed: Feb. 28, 1995

[51] Int. Cl.⁶ .................................................. A01N 43/08
[52] U.S. Cl. ............................................ 514/474; 514/449
[58] Field of Search ..................................... 514/474, 449

[56] References Cited

U.S. PATENT DOCUMENTS

| | | | |
|---|---|---|---|
| 5,032,610 | 7/1991 | Borretzen et al. | 514/467 |
| 5,036,103 | 7/1991 | Kochi | 514/467 |
| 5,117,972 | 5/1992 | Ohwishi | 514/530 |
| 5,130,145 | 7/1992 | Oftebro et al. | 424/649 |
| 5,135,948 | 8/1992 | Borretzen et al. | 514/474 |

OTHER PUBLICATIONS

Riordan, N. et al; Intravenous Ascorbate as a tumor cytotoxic chemotherapeutic agent, Mar. 1995 Journal of Medical Hypothesis.

Primary Examiner—Nathan M. Nutter
Assistant Examiner—Michael A. Williamson
Attorney, Agent, or Firm—Philip J. Lee

[57] ABSTRACT

A method of treating cancer in a patient by raising and maintaining the concentration of ascorbic acid, or ascorbate, in the patient's plasma to at least the level expected to be toxic to an in vitro culture of cells of the type of cancer being treated, the required plasma ascorbate levels being achieved and maintained using long term intravenous infusions of large amounts of ascorbate, with or without ascorbate cytotoxicity effectiveness enhancing or tumor site delivery and absorption enhancing agents.

32 Claims, No Drawings

THERAPEUTIC METHOD FOR THE TREATMENT OF CANCER

BACKGROUND OF THE INVENTION

A. Field of invention

The present invention relates generally to methods of therapeutically treating cancer and more particularly to a new and improved method of administering ascorbic acid as a therapeutic agent.

B. Description of Related Art

In the treatment of cancer, surgical intervention may, in some cases, be effective, but it is generally understood that an effective method of treating malignancies on a cellular basis is desirable. A frequently used treatment mode for malignant tumors is the administration of a chemical agent that is selectively toxic to the neoplastic cells within the tumor, without being prohibitively toxic to the patient in general. A number of such agents have been used and are being used with varying degrees of success, but in general the successful use of such known chemotherapeutic agents is restricted by the toxicity of the agent and the corresponding side effects to the patient. Due to the limited effectiveness of such known agents, none of the known treatments qualifies as a satisfactory treatment for the condition. While a number of schemes for reducing the side effects of administering such chemotherapeutic agents have and are being studied and being attempted, including selective site delivery systems, such schemes have not succeeded to the point of eliminating the need for an agent that is more selectively toxic.

Known adverse side effects of administration of known chemotherapeutic agents include hair loss, nausea and vomiting, cardiac toxicity and secondary cancers, as well as bone marrow suppression leading to immune suppression and hematopoietic dysfunctions. A side effect of immunological suppression is particularly undesirable because of infectious complications in an immune suppressed patient can be severe and even fatal.

It is known that ascorbic acid and salts thereof have shown a cytotoxic effect when administered in vitro to tumor cell lines. For the purposes of this application, a reference to ascorbic acid includes the anionic component, ascorbate whether as an acid or one of the pharmaceutically acceptable salt thereof, most notably including sodium ascorbate and calcium ascorbate, any of which are included in a reference to "ascorbic acid" or "ascorbate". The cytotoxic effect of ascorbic acid is understood to relate to the increased production of intracellular hydrogen peroxide, which is more toxic to tumor cells due to the lower levels of catalase typically present in tumor cells as compared to normal cells. Although some cancers may respond to lower levels, the concentration level of ascorbic acid required for in vitro cytotoxic effectiveness are normally in the range of 5–40 mg/dl with concentrations of 30–40 mg/dl being typical. Since normal plasma levels of ascorbic acid range from 0.39–1.13 mg/dl and the highest levels generally achievable in humans by oral supplementation is 4.5 mg/dl, it has not been known how cytotoxically effective levels of ascorbic acid could be achieved in vivo, and whether the dosage required to attain such levels could be safely administered. Moreover, since ascorbic acid is readily cleared from the body, the tumor cytotoxic effect, if any, achieved by conventionally administered doses of ascorbic acid would be transitory at best.

At least two studies have found a failure of high doses of ascorbic acid to have the desired effect in the treatment of cancer, namely: Creagan, E. T.; Moertel, C. G.; O'Fallon, J. R.; et al. *Failure of High Dose Vitamin C (ascorbic acid) to Benefit Patients With Advanced Cancer: A Control Trial.* N Engl. J. Med., 1979; 301:687–690 and Mortel, C. G.; Fleming, T. R.; Creagan, E. T.; , et al. *High Dose of Vitamin C Versus Placebo In The Treatment of Patients With Advanced Cancer Who Have Had No Prior Chemotherapy.* N Engl. J. Med., 1985; 312:137–141. Heretofore the highest dosage understood to be safely administered to a human was approximately 10–15 grams. It is believed that the reported results demonstrate that oral administration of doses in the 10–15 gram range, considered maximum safe dosage, does not achieve cytotoxic levels of ascorbic acid in the patient's blood and that those reported beneficial effects of such dosages are the result of the increase in collagen which serves to isolate the neoplasm in cancer patients, due to the function of ascorbic acid as a cofactor in the enzymatic hydroxylation of proline residues of collagen to form hydroxyproline residues. The generally slight, marginal or negative results demonstrate that there was little or no direct cytotoxic effect of the ascorbic acid administered to the tumor cells in prior in vivo studies. The positive results are believed to have been achieved by means of increased stromal resistance to the invasiveness of the malignancies studied, although the lack of monitoring of the level of ascorbic acid present in the plasma prevents an accurate assessment.

There have been reports of rare instances of wide-spread tumor necrosis and hemorrhage in rare cases of extreme tumor sensitivity to ascorbic acid. Such results are not only rare but, being fatal, do not argue for the use of ascorbic acid as a therapeutic agent. In addition, it is known that the cytotoxic effect of ascorbic acid is diminished, to varying degrees, by the exposure to plasma. Therefore, the in vitro results are not readily duplicated in vivo and the concentrations of ascorbic acid that are effectively toxic in vitro are not as effective, nor as easy to achieve, in test subjects.

The prior studies related to ascorbic acid in cancer therapy, have not demonstrated that tumor-toxic ascorbic acid plasma levels could be achieved. Most of the prior art used oral ascorbate as an adjunct to other therapeutic options. Although some describe the use of intravenous ascorbate, the purpose was simply to deliver the dosage rather manipulate the plasma concentration over time, and therefore no effort has been made to measure plasma levels and no treatment has been described based upon maintenance of those levels at a concentration high enough to be cytotoxic to tumor cells continued over a significant period of time.

SUMMARY OF THE INVENTION

The method of the present invention comprises the treatment of cancer by administering sufficient amounts of ascorbic acid to raise the concentration of ascorbic acid in the patient's plasma above a level that is cytotoxic to the cancer tumor cells. The treatment is based on the fact that tumor cells contain between 10 and 100 fold less of the enzyme catalase than normal cells. Catalase converts toxic hydrogen peroxide to non-toxic oxygen and water. This biochemical difference between normal and tumor cells provides a window of opportunity for selective toxicity. It has been known for some time that ascorbate is capable of inducing the intracellular production of hydrogen peroxide. The basis of the present invention is the discovery, through experimentation, that concentrations of ascorbate capable of inducing toxic reactions in tumor cells were achievable in vivo through intravenous infusion of large amounts of ascorbic acid in solution. The dosage of ascorbic acid provided in the present method are well in excess of the levels conventionally thought to be toxic and have been administered without reported detrimental side effects. Since serum demonstrates an unquantified tendency toward reduction in cytotoxic effectiveness of ascorbic acid, there is not a direct translation of in vitro to in vivo results. For this reason, it is desirable to exceed the levels required for in vitro cytotoxicity in tumor cells by a wide margin. It is also advantageous to maintain the cytotoxic level of ascorbic acid in the patient's plasma for as long a period of time as is reasonably possible. To achieve such results in patients, the treatment has required intravenous administration of as much as 115 grams of ascorbic acid infused over several hours to achieve an apparently effective level of ascorbic acid. The initial treatment involved infusion periods of 8 hours and the duration of infusion may be lengthened as it has been found that benefits increase with the duration of the cytotoxic plasma levels. It has been found that repeated infusions are necessary to overcome the patient's ability to destroy the ascorbic acid administered. Continuous administration of a solution of ascorbic acid maintains the plasma levels despite the bodies ability to clear the ascorbate from the patient's system. Continuation of the treatment over multiple infusions is believed to be desirable. Oral supplementation in addition to infusion of ascorbic acid has been found to avoid abnormally low levels of ascorbic acid between infusions as has been suggested would result from a scorbutic rebound. The plasma levels of ascorbic acid in patients are routinely and repeatedly monitored throughout the treatment and the amount of ascorbic acid administered is adjusted according to the individual patient's tolerance and the target level of ascorbic acid. Target levels of ascorbic acid are set according to the type of cancer afflicting the patient using in vitro studies of cytotoxicity in similar cell lines. More accurate target levels can be achieved by in vitro experimentation of malignant cells taken from the patient if such are available. A further development of the treatment of the present invention involves the direct testing of the cytotoxic effectiveness of the patient's serum. Serum is drawn during the infusion and either the patient malignant cells, if available, or similar cell lines are exposed to the patient's serum with the effects observed. This direct testing provides information that is used to adjust the amount of ascorbic acid administered to ensure that effective plasma levels have been achieved.

The treatment can include the additional administration of agents that are known to act synergistically with ascorbate in the intracellular generation of hydrogen peroxide. The combination of ascorbic acid and such agent effective in increasing hydrogen peroxide production with a drug delivery system that can selectively deliver the drugs to the site of the tumor is expected to increase the effectiveness of the treatment and lower the plasma levels of ascorbic acid required for an effective treatment.

The ascorbic acid infusion process has been found to result in the depletion of certain minerals and other substances. Such depletions are remedied by supplementation as required throughout the course of the treatment.

DETAILED DESCRIPTION OF THE INVENTION

The method which is the subject of the present invention comprises a means for treating cancer by achieving and maintaining concentrations of ascorbic acid in the patient's plasma which are high enough to be cytotoxic to tumor cells, and in particular those cancer cells afflicting the patient.

Again it is noted that a reference to "ascorbic acid" includes the anionic component, ascorbate, whether present as an acid or one of the pharmaceutically acceptable salts thereof including, but not limited to, sodium ascorbate and calcium ascorbate.

Since, as stated above, there is not a direct translation of in vitro to in vivo results, the level of ascorbic acid within the patient's plasma must be raised to exceed the levels required for in vitro cytotoxicity in tumor cells and maintained at that level for a significant period of time. The patient undergoes an intravenous infusion of ascorbic acid in a medically acceptable aqueous solution such as Ringer's lactate. As an example, Mr. X whose case is described below was administered 115 grams of ascorbic acid in 1000 cc Ringer's lactate, infused over 8 hours. The infusions are continued until resolution of the patient's tumors have been evidenced. Normal diagnosis and classification of the patient's cancer can be used in conjunction with experimental results to predict the target levels of ascorbic acid for an effective treatment. More accurate target levels can be achieved by experimentation on cultured malignant cells taken from the patient if such are available. Verification of the cytotoxic effectiveness of the patient's serum at specified levels of ascorbic acid is obtained by direct observation of the effect of samples of the patient's serum on the patient's malignant cells or similar cells. During the infusion, when the target plasma level of ascorbic acid has been achieved, serum samples are drawn and appropriate cell cultures are exposed to the serum samples to determine whether the desired level of tumor cytotoxicity has been reached. If necessary, the target levels and the infusion dosage and rate can be adjusted as may be suggested by the effectiveness of the serum samples. The plasma levels of ascorbic acid in patients are routinely and repeatedly monitored throughout the treatment and the amount of ascorbic acid administered is adjusted according to the individuals tolerance and the target level of ascorbic acid. As an example, during the fourth infusion of Mr. X, the patient's plasma level of ascorbic acid was raised to 158 mg/dl by one hour and to 185 mg/dl by the fifth hour of the fourth eight hour infusion. Mr. X has received 39 8 hour infusions of ascorbic acid ranging in dose from 57.5 grams to 115 grams per infusion over a period of 13 weeks, without reported detrimental side effects.

In addition to the intravenous infusions of ascorbic acid, oral supplementation of ascorbic acid at dosage levels determined by the patient's tolerance is used to avoid abnormally low levels of ascorbic acid between infusions.

The method further comprises the supplemental administration (either orally, intramuscularly, or intravenously) of molecules which can be depleted from the body when high-dose ascorbate is administered. These molecules include the amino acids cysteine and methionine, and metals, such as calcium, magnesium, copper, zinc, iron, molybdenum, and selenium. Of these agents, copper and iron are understood to have a role in increasing the tumor cytotoxic effectiveness of the ascorbate The treatment can include the additional administration of agents that are known to act synergistically with ascorbate in the intracellular generation of hydrogen peroxide. Agents known to act synergistically with ascorbate in the production of hydrogen peroxide include: vitamin K, and the synthetic water soluble form of vitamin K, menadione; long chain polyunsaturated fatty acids including linolenic acid, linoleic acid, arachidonic acid, eicosapentaenoic acid, dihomogamma-linoleic acid, docosahexaenoic acid, and eicosatetraenoic acid; hydrogen peroxide; azide containing molecules, including the azide salt, sodium azide; and certain metals, such as copper and iron.

It is further expected that the combination of ascorbic acid alone or with a hydrogen peroxide production enhancing agent with a drug delivery system that can selectively deliver the drugs to the site of the tumor will increase the effectiveness of the treatment and lower the plasma levels of ascorbic acid required for an effective treatment. One such drug delivery molecule is hyaluronic acid which was found to be preferentially bound by the molecule "intracellular adhesion molecule-1" (1CAM-1). ICAM-1 is found in greater than normal concentrations at sites of inflammation and in and around tumor tissue. The combination of ascorbate alone or with peroxidation potentiators and hyaluronic acid would be expected to concentrate the tumor cytotoxic agents at the site of the tumor. The chemical combination of ascorbate with a drug delivery molecule such as HA would be expected to bring about a similar result if the ascorbate/drug delivery bond is sufficiently weak that the ascorbate could be released at the tumor.

The combination of ascorbic acid with quercetin, which is a bioflavonoid, or similar molecules with similar properties including ease of transmembrane transfer will enhance the transmembrane transfer of ascorbic acid and thus increase the tumor toxic effect of the ascorbic acid.

The method further comprises the supplemental administration (either orally, intramuscularly, or intravenously) of agents which optimize the conditions necessary in the body for the production and maintenance of high molecular weight hyaluronic acid, including the administration of high molecular weight HA directly. Agents which aid in the optimization of high molecular weight HA include: thiamine, cysteine, vitamin B6, pantothenic acid, glucosamine sulfate, and glucuronic acid.

Case Histories

The following case histories are descriptions of actual patients and the treatment of the patients in accordance with the method of the present invention and are presented as examples of the method of the present invention and as evidence of the efficacy of the treatment, and not to limit or imply a limitation of the invention to the specific details of treatment described below:

1. Mr. X is a 68 year old male with metastatic carcinoma of the head of the pancreas. After a debulking operation, a considerable amount of the tumor mass found to be inoperable (2×2×4 cm). Several eight hour intravenous infusions of ascorbate were required until a plasma level of ascorbate exceeding 150 mg/dl was achieved. The dose required to maintain the plasma level above 150 mg/dl was then infused 3 times weekly for 4 weeks. Lower doses were then administered 3 times weekly for 3 months. Six months after diagnosis, there was no detectable tumor seen on a C-T scan.

2. Mr. Y is a 47 year old male with metastatic fibrous histiocytoma. Three metastatic lesions to the lungs were initially presented, as revealed by chest x-ray. Two masses were in the left lung and one mass was in the right lung. All masses measured approximately 2 cm. in diameter. Plasma levels of 110 mg/dl of ascorbate were achieved with intravenous infusions of ascorbate. After seven months of therapy, a chest x-ray revealed that the right lung mass had disappeared and one of the left lung masses had decreased in size (to about 1 cm) with decreased radio-opacity. After twelve months of therapy, the left lung mass which had regressed was completely resolved. There had been no change in the size of the remaining left lung metastasis after twelve months of therapy.

3. Mr. Z is a 29 year old male with metastatic colon carcinoma. Cancer was discovered during exploratory surgery. Multiple metastases were found on the omentum, transverse and sigmoid colon, and the peritoneum. Biopsy samples from these metastases were obtained during surgery and most of the tumor mass was not removed. A cell culture line was established from the tissue biopsies, and the patient tumor cells were tested to determine the sensitivity of the tumor cells to ascorbic acid. An ascorbate concentration of 30 mg./dl. was found to be toxic to 100 percent of the patient's tumor cells. A target level of plasma concentration of ascorbic acid was selected at three times the level found to be toxic to the patient's tumor cells. Intravenous ascorbate was begun and the infusion quantity and rate required to achieve and maintain the targeted plasma ascorbic acid concentration of 90 mg/dl was determined. Twenty hour infusions of ascorbate were given three times per week. After four months of therapy, a surgical ileostomy was performed due to chronic diarrhea. During surgery, the multiple metastases were observed to have decreased significantly in size and have a flaccid consistency.

4. Ms. W is a 60 year female with metastatic ovarian cancer. After six months of standard chemotherapy, a second exploratory surgery was performed, at which time metastases throughout the abdominal cavity were found. The patient was started on intravenous ascorbate infusions at the quantity and rate of flow required to maintain a plasma concentration of 80 mg/dl. The patients level of cancer antigen CA-125 which had been elevated from the time of diagnosis and throughout most of the chemotherapy regimen returned to normal and remained within normal limits throughout her intravenous ascorbate therapy for the next seven months.

5. Mr. U was a 73 year old male with metastatic prostate cancer. A baseline blood sample was drawn from the patient and the serum was separated. An intravenous infusion of 105 grams of ascorbate was performed over 5 hours. At the and of the 5 hours another blood sample was taken and again the serum was separated. The pre-infusion serum sample was assayed and found to contain an ascorbic acid concentration of 3.4 mg/dl and the post-infusion serum samples were assayed and found to contain an ascorbic acid concentration of 165 mg/dl. The cytotoxic effectiveness of both serum samples was tested against a line of human prostate tumor cells called "PC-3"from American Type Culture Collection. The PC-3 cells were plated, 3,000 cells per well in plastic 96 well tissue culture plates 24 hours before the blood was taken from the patient above. 100% and 50% (diluted with complete culture medium, DMEM) serum solutions from both samples were added to 16 wells each of the PC-3 cells which had been plated earlier. After a five day incubation, the number of surviving tumor cells in the wells containing the 100% and 50% solutions of the post-infusion serum sample was compared to the number of surviving tumor cells in the wells containing the 100% and 50% solutions of the pre-infusion serum sample and the percent survival was calculated as follows:

|                                                              | percent tumor cell survival |
| ------------------------------------------------------------ | --------------------------- |
| Preinfusion serum (3.4 mg/dl Ascorbic acid) serum concentration |                             |
| 50%                                                          | 100                         |
| 100%                                                         | 100                         |
| Post-infusion serum (165 mg/dl Ascorbic acid) serum concentration |                             |
| 50%                                                          | 15                          |
| 100%                                                         | 19                          |

The foregoing results demonstrate that a beneficial level of tumor cytotoxic effectiveness can be achieved by the elevation of ascorbic acid concentration in the tumor patient's serum by means of the intravenous infusion of ascorbic acid.

While the preferred constituents and method of the foregoing invention have been set forth for purposes of illustration, the foregoing description should not be deemed a limitation of the invention herein. Accordingly, various modifications, adaptations and alternatives may occur to one skilled in the art without departing from the spirit and the scope of the present invention.

What is claimed is:

1. A method of treating cancer in patients consisting essentially of the step of administering to the patient, by intravenous infusion, an anti-cancer effective dose of ascorbic acid or a pharmaceutically acceptable salt thereof.

2. The method of claim 1, wherein the intravenous infusion of ascorbic acid or a pharmaceutically acceptable salt thereof is administered over a period of at least two hours.

3. The method of claim 2, further comprising the step of determining the serum concentration of ascorbic acid that is effectively cytotoxic to malignant cells similar to those afflicting the patient.

4. The method of claim 3 further comprising the step of combining with the ascorbic acid, a tumor delivery agent.

5. The method of claim 3 further comprising the step of combining with the ascorbic acid, effective amounts of at least one hydrogen peroxide producing agents selected from a group substantially consisting of vitamin K, menadione, linolenic acid, linoleic acid, arachidonic acid, eicosapentaenoic acid, dihomogamma-linoleic acid, docosahexaenoic acid, eicosatetraenoic acid, hydrogen peroxide, sodium azide, copper, and iron.

6. The method of claim 5 wherein the ascorbic acid and hydrogen peroxide production enhancing agent are combined with tumor delivery effective amounts of hyaluronic acid.

7. The method of claim 6 wherein the ascorbic acid and the hydrogen peroxide production enhancing agent are combined with effective amounts of high molecular weight hyaluronic acid.

8. The method of claim 7 further comprising the step of administering deficiency reducing effective amounts of cysteine, methionine, calcium, magnesium, copper, zinc, iron, molybdenum, and selenium.

9. The method of claim 2 further comprising the step of combining with the ascorbic acid, effective amounts of at least one hydrogen peroxide producing agents selected from a group substantially consisting of vitamin K, menadione, linolenic acid, linoleic acid, arachidonic acid, eicosapentaenoic acid, dihomogamma-linoleic acid, docosahexaenoic acid, eicosatetraenoic acid, hydrogen peroxide, sodium azide, copper, and iron.

10. The method of claim 9 further comprising the step of administering an effective amount of at least one high molecular weight hyaluronic acid production enhancing agent selected from a group consisting of thiamine, cysteine, vitamin B6, pantothenic acid, glucosamine sulfate, and glucuronic acid.

11. The method of claim 1, wherein the intravenous infusion of ascorbic acid or a pharmaceutically acceptable salt thereof is administered over a period of at least eight hours.

12. The method of claim 11 further comprising the steps of determining the cytotoxicity of the concentration of ascorbic acid in the patient's serum by direct in vitro test using malignant cells similar to those afflicting the patient, and adjusting the patient's serum concentration to equal or exceed the level determined to be effectively cytotoxic to said malignant cells.

13. A method of treating cancer in human patients consisting essentially of the following steps:

A. determining a target concentration of ascorbic acid that is cytotoxic to malignant cells of, or similar to, the cancer afflicting a patient by observing the cytotoxic effect of ascorbic acid upon an in vitro culture of the patient's malignant cells or cells similar to those afflicting the patient; and B. raising the concentration of ascorbic acid in a patient's blood to, and maintaining the ascorbic acid concentration at, at least equal to the target concentration by intravenous infusion of a solution containing sufficient ascorbic acid or a pharmaceutically acceptable salt thereof.

14. The method of claim 13, wherein the target concentration of ascorbic acid in the patient's blood is maintained for at least two hours.

15. The method of claim 14 further comprising the step of combining with the ascorbic acid, effective amounts of at least one hydrogen peroxide producing agents selected from a group substantially consisting of vitamin K, menadione, linolenic acid, linoleic acid, arachidonic acid, eicosapentaenoic acid, dihomogamma-linoleic acid, docosahexaenoic acid, eicosatetraenoic acid, hydrogen peroxide, sodium azide, copper, and iron.

16. The method of claim 14 further comprising the step of combining with the ascorbic acid, tumor delivery effective amounts of hyaluronic acid.

17. The method of claim 15 wherein the ascorbic acid and hydrogen peroxide production enhancing agent are combined with tumor delivery effective amounts of hyaluronic acid.

18. The method of claim 14 further comprising the step of administering an effective amount of at least one high molecular weight hyaluronic acid production enhancing agent selected from a group consisting of thiamine, cysteine, vitamin B6, pantothenic acid, glucosamine sulfate, and glucuronic acid.

19. The method of claim 14 further comprising the step of administering deficiency reducing effective amounts of cysteine, methionine, calcium, magnesium, copper, zinc, iron, molybdenum, and selenium.

20. The method of claim 13, wherein the tumor cytotoxic concentration of ascorbic acid in the patient's blood is maintained for at least eight hours.

21. The method of claim 20, further comprising a plurality of iterations of the step of raising the patient's serum concentration of ascorbic acid.

22. The method of claim 13, wherein the step of determining a target concentration of ascorbic acid further comprises determining the cytotoxicity of the concentration of ascorbic acid in the patient's serum by exposing a culture of the patient's malignant cells to a solution of the patient's serum.

23. A method of treating cancer in human patients comprising the following steps:
  A. determining the serum concentration of ascorbic acid that is effectively cytotoxic to malignant cells similar to those afflicting the patient, and
  B. administering to the patient, by intravenous infusion over a period of at least two hours, the following, in combination with tumor delivery effective amounts of hyaluronic acid:
    1. an anti-cancer effective dose of ascorbic acid or a pharmaceutically acceptable salt thereof, and
    2. effective amounts of at least one hydrogen peroxide producing agent selected from a group substantially consisting of vitamin K, menadione, linolenic acid, linoleic acid, arachidonic acid, eicosapentaenoic acid, dihomogamma-linoleic acid, docosahexaenoic acid, eicosatetraenoic acid, hydrogen peroxide, sodium azide, copper, and iron.

24. The method of claim 23 wherein the hyaluronic acid is of high molecular weight.

25. The method of claim 24 further comprising the step of administering deficiency reducing effective amounts of cysteine, methionine, calcium, magnesium, copper, zinc, iron, molybdenum, and selenium.

26. A method of treating cancer in human patients consisting essentially of the following steps:
  A. determining a target concentration of ascorbic acid that is cytotoxic to malignant cells of, or similar to, the cancer afflicting a patient by observing the cytotoxic effect of ascorbic acid upon an in vitro culture of the patient's malignant cells or cells similar to those afflicting the patient; and
  B. raising the concentration of ascorbic acid in a patient's blood to, and maintaining, for at least two hours, the ascorbic acid concentration at, at least equal to the target concentration by intravenous infusion of a solution containing sufficient ascorbic acid or a pharmaceutically acceptable salt thereof and tumor delivery effective amounts of hyaluronic acid.

27. The method of claim 26 further comprising the step of combining with the ascorbic acid, effective amounts of at least one hydrogen peroxide producing agents selected from a group substantially consisting of vitamin K, menadione, linolenic acid, linoleic acid, arachidonic acid, eicosapentaenoic acid, dihomogamma-linoleic acid, docosahexaenoic acid, eicosatetraenoic acid, hydrogen peroxide, sodium azide, copper, and iron.

28. The method of claim 26 further comprising the step of administering an effective amount of at least one high molecular weight hyaluronic acid production enhancing agent selected from a group consisting of thiamine, cysteine, vitamin B6, pantothenic acid, glucosamine sulfate, and glucuronic acid.

29. The method of claim 26 further comprising the step of administering deficiency reducing effective amounts of cysteine, methionine, calcium, magnesium, copper, zinc, iron, molybdenum, and selenium.

30. The method of claim 26, wherein the tumor cytotoxic concentration of ascorbic acid in the patient's blood is maintained for at least eight hours.

31. The method of claim 30, further comprising a plurality of iterations of the step of raising the patient's serum concentration of ascorbic acid.

32. The method of claim 26, wherein the step of determining a target concentration of ascorbic acid further comprises determining the cytotoxicity of the concentration of ascorbic acid in the patient's serum by exposing a culture of the patient's malignant cells to a solution of the patient's serum.

* * * * *